US006735278B2

United States Patent
Madsen et al.

(10) Patent No.: US 6,735,278 B2
(45) Date of Patent: May 11, 2004

(54) METHOD AND APPARATUS FOR X-RAY DIFFRACTION ANALYSES

(75) Inventors: Ian Charles Madsen, Clayton South (AU); Nicola Vivienne Yorke Scarlett, Elsternwick (AU); Constantine George Manias, Unley Park (AU); David James Retallack, Hawthorn (AU); Karl Edmund Schneider, Croyden Park (AU)

(73) Assignee: FCT - Actech PTY LTD (AU)

( * ) Notice: Subject to any disclaimer, the term of this patent is extended or adjusted under 35 U.S.C. 154(b) by 156 days.

(21) Appl. No.: 10/024,930

(22) Filed: Dec. 19, 2001

(65) Prior Publication Data

US 2002/0094060 A1 Jul. 18, 2002

Related U.S. Application Data

(63) Continuation of application No. PCT/AU00/00697, filed on Jun. 21, 2000.

(30) Foreign Application Priority Data

Jun. 21, 1999 (AU) .............................................. PQ1094

(51) Int. Cl.[7] .............................................. G01N 23/20
(52) U.S. Cl. .......................................... 378/79; 378/71
(58) Field of Search .............................. 378/71, 79, 75, 378/53, 58, 83, 86

(56) References Cited

U.S. PATENT DOCUMENTS 3,980,882 A 9/1976 Carr-Brion et al.
5,272,745 A * 12/1993 Smallbone .................... 378/47
5,627,874 A * 5/1997 Smallbone .................. 378/208
6,072,853 A * 6/2000 Hall ............................ 378/73

FOREIGN PATENT DOCUMENTS

| ES | 2 134 680 | 10/1999 |
|---|---|---|
| FR | 2 754 062 | 4/1998 |
| WO | WO-99/46584 | 9/1999 |

OTHER PUBLICATIONS

Patent Abstracts of Japan, JP 8–259287 A (Chichibu Onoda Cement Corp.) Oct. 8, 1996.

* cited by examiner

Primary Examiner—Craig E. Church
Assistant Examiner—Jurie Yun
(74) Attorney, Agent, or Firm—Lerner, David, Littenberg, Krumholz & Mentlik, LLP

(57) ABSTRACT

A method and apparatus for continuously presenting a sample from a stream of particulate material which contains crystalline substances and for effectively continuously analysing the sample by X-ray diffraction are provided. An extracted sample flow is fed onto a continuously moving carrier and its surface smoothed and flattened for X-ray diffraction patterns to be detected and analysed to provide a compositional analysis for the crystalline substances. The sample is continuously removed from the carrier prior to further sample being fed onto the carrier. The invention is particularly applicable for phase composition analysis of cement and cement clinker and provides an effectively continuous analysis substantially in real time in contrast to prior art laboratory analyses of discrete samples.

23 Claims, 2 Drawing Sheets

FIG 2

Sample BH-T2-67 sample date 9-11/5/99 115 C

| Date | Time | Batch No. | R Factor | CaO | SiO₂ | Al₂O₃ | Ferrite-a | Ferrite-b | Belite | Alite | Aluminate | Lime | Portlandit | Gypsum | Hemihydr | Anhydrite |
|---|---|---|---|---|---|---|---|---|---|---|---|---|---|---|---|---|
| 5/12/99 | 11.51 | 12599 | 11.592 | 65.384 | 20.063 | 5.102 | 5.082 | 8.213 | 7.398 | 65.113 | 0.129 | 0.069 | 1.562 | 3.052 | 2.273 | 0.001 |
| 5/12/99 | 11.53 | 12599 | 11.81 | 65.454 | 19.903 | 5.178 | 6.664 | 6.254 | 6.142 | 65.72 | 0.147 | 0.222 | 0.691 | 3.323 | 2.414 | 0 |
| 5/12/99 | 11.54 | 12599 | 11.657 | 65.212 | 19.626 | 5.064 | 6.684 | 6.089 | 6.299 | 66.521 | 0.005 | 0.068 | 0.667 | 3.224 | 2.228 | 0 |
| 5/12/99 | 11.56 | 12599 | 11.733 | 65.362 | 19.874 | 5.052 | 5.67 | 7.475 | 5.894 | 66.594 | 0.347 | 0 | 1.061 | 3.05 | 2.595 | 0.01 |
| 5/12/99 | 11.57 | 12599 | 11.72 | 65.504 | 19.83 | 5.336 | 5.186 | 8.161 | 5.583 | 66.986 | 0.175 | 0.123 | 0.841 | 3.101 | 2.199 | 0 |
| 5/12/99 | 11.59 | 12599 | 11.557 | 65.628 | 19.848 | 5.417 | 5.036 | 7.797 | 6.427 | 67.596 | 0.203 | 0.074 | 1.241 | 2.845 | 1.998 | 0 |
| 5/12/99 | 12.00 | 12599 | 11.547 | 65.77 | 20.177 | 5.021 | 5.079 | 7.88 | 6.328 | 67.136 | 0.315 | 0.284 | 1.008 | 2.981 | 1.613 | 0 |
| 5/12/99 | 12.02 | 12599 | 11.574 | 65.776 | 20.08 | 5.231 | 6.188 | 6.047 | 7.87 | 65.474 | 0.005 | 0.124 | 1.425 | 3.107 | 2.203 | 0.01 |
| 5/12/99 | 12.03 | 12599 | 11.877 | 65.002 | 20.071 | 4.865 | 5.801 | 7.051 | 6.436 | 67.384 | 0.007 | 0.098 | 0.702 | 2.977 | 1.799 | 0.002 |
|  |  |  | 12.243 | 65.752 | 20.187 | 5.271 |  |  |  |  |  |  |  |  |  |  |

| Calcite | Quartz | Fe₂O₃ | MgO | TiO₂ | SO₃ | Na₂O | K₂O | Loss |
|---|---|---|---|---|---|---|---|---|
| 0.001 | 0.418 | 3.745 | 1.009 | 0.14 | 2.897 | 0.173 | 0.221 | 0.952 |
| 0.093 | 0.345 | 3.801 | 1.007 | 0.142 | 2.674 | 0.178 | 0.231 | 1.2 |
| 1.429 | 0.448 | 3.705 | 0.996 | 0.138 | 2.877 | 0.172 | 0.216 | 1.642 |
| 1.075 | 0.424 | 3.683 | 0.997 | 0.137 | 2.728 | 0.173 | 0.217 | 1.448 |
| 0.015 | 0.135 | 3.798 | 1.015 | 0.141 | 2.856 | 0.187 | 0.227 | 1.064 |
| 0.093 | 0.079 | 3.849 | 1.025 | 0.143 | 2.655 | 0.19 | 0.227 | 1.031 |
| 0.007 | 0.454 | 3.697 | 1.006 | 0.137 | 2.425 | 0.169 | 0.216 | 1.024 |
| 0.045 | 0.433 | 3.753 | 1.014 | 0.139 | 2.276 | 0.182 | 0.228 | 0.989 |
| 0.787 | 0.372 | 3.561 | 0.975 | 0.131 | 2.666 | 0.169 | 0.224 | 1.479 |
| 0.053 | 0.272 | 3.744 | 1.014 | 0.138 | 2.378 | 0.186 | 0.229 | 0.929 |

METHOD AND APPARATUS FOR X-RAY DIFFRACTION ANALYSES

CROSS-REFERENCE TO RELATED APPLICATIONS

The present application is a continuation of International Application No. PCT/AU00/00697, which was filed in the English language on Jun. 21, 2000.

FIELD OF THE INVENTION

The present invention relates to a method and apparatus for continuously presenting a sample from a stream of particulate material which contains crystalline substances and effectively continuously analysing the sample by X-ray diffraction (XRD). More particularly, the present invention relates to phase composition analysis of cement and cement clinker and will be described in relation to this application, however it is to be understood the invention is applicable for analysing other materials which include crystalline substances, such as for example from mineral processing streams.

BACKGROUND OF THE INVENTION

In the manufacture of cement, feedstock materials such as limestone, shale, sand and iron oxide are blended, milled and then fired in a kiln from which cement clinker is derived. The cement clinker with some additives, is then milled to produce cement. The milling, which is the final stage in manufacturing cement, is usually carried out in a ball mill, ie a rotary mill which contains a charge of steel balls. As the mill rotates the input materials (mainly cement clinker and small amounts of additives such as gypsum, limestone and sometimes fly ash) are ground and mixed to a fine state or powder.

X-ray diffraction measurements may be made on the cement clinker from the kiln, the clinker being suitably cooled and crushed to a fine powder for the measurements. Such measurements can provide information on the ratios between the different clinker phases and on the percentage of free lime. The strength of a final cement product is significantly determined by these phase ratios, and the amount of free lime is an indicator of the degree of burning in the kiln. Furthermore, the mineralogical composition can provide information regarding temperature profiles in the kiln, and indicate deviations from the optimum. Thus such X-ray diffraction measurements, if available on line, would provide information which can be used to control the kiln operation, burner adjustment and hence product quality.

X-ray diffraction measurements may also be made on the cement powder from the cement finish mill. These can provide information on the ratios of gypsum and other additives in the cement, information about crystal phases in the cement clinker, information on free lime and portlandite (prehydration) and on the degree of dehydration of the gypsum. Such ratios also affect the strength of the final cement product and the degree of gypsum dehydration affects the cement setting time. Thus, if these measurements were available on-line, information would be provided which can be used to control the milling and thus the quality of the final cement product. By way of example, the hydration states of gypsum in conjunction with the free lime and calcium aluminate content and form can be used to predict setting times. Furthermore, the finish mill operating temperature can be used to adjust the gypsum dehydration and hence control setting times. By way of further example, the mineralogical composition can be used to predict the strength development of cement product. The composition and fineness of the cement can then be adjusted to provide a target cement strength.

Heretofore to the applicant's knowledge, X-ray diffraction measurements of ex-kiln cement clinker and ex-mill cement powder have generally been laboratory based. For such measurements, a sample of the process stream, which may be taken automatically or by hand, is delivered to the laboratory where individual sample pellets, of the order of only a few grams, are prepared and presented to the XRD machine, either by hand or using robotics. The time taken for such sample preparation and measurement limits the usefulness of the information for process control. Furthermore, the extra grinding required to reduce the particle size to enable static samples to be analysed by the X-ray analysis may cause changes in the dehydration states for milled cement.

SUMMARY OF THE INVENTION

According to a first aspect, the present invention provides a method for analysing a stream of particulate material containing crystalline substances including (i) extracting a sample flow from the stream of particulate material, (ii) preparing the sample flow for X-ray diffraction measurements and conveying the so prepared sample flow through a measurement station, (iii) directing an X-ray beam onto the sample flow as it passes through the measurement station and detecting diffracted X-rays over an angular range to provide a diffraction pattern, (iv) analysing the diffraction pattern to determine a composition for crystalline substances in the sample, (v) repeating step (iii) to provide diffraction patterns from the continuously moving sample at predetermined intervals, and (vi) repeating step (iv) for each diffraction pattern from step (v), whereby a series of sequential composition determinations from the sample flow are provided which represent the composition of crystalline substances in the stream of particulate material.

It will be appreciated that the above described method can provide a wide angular range diffraction pattern at short intervals from a continuously moving sample. The series of sequential composition determinations from such patterns represents the composition of the stream of particulate material substantially in real time. The series of composition determinations also gives effectively a "continuous" analysis of the stream of particulate material (the term "continuous" in this context meaning continuing discrete compositional determinations separated by short time intervals).

Preferably the diffracted X-rays of step (iii) are simultaneously detected over the angular range.

Preferably the diffraction patterns are analysed using a whole pattern analysis method, for example the Rietveld method.

Preferably step (ii) includes feeding the sample onto a continuously moving carrier and smoothing and flattening its surface and more preferably the sample is formed into a bed on the moving carrier. Preferably the carrier includes an endless groove for receiving the sample and into which the sample is preferably packed to form the bed. The preparation of the sample flow is to ensure that the sample surface is presented to the measurement station at a constant height.

Following step (iii) the sample is continuously removed from the carrier prior to feeding further sample onto the carrier.

Using this invention, extra grinding of an ex-mill cement sample is not required because the moving sample presented to an X-ray diffraction machine ensures that even with larger particle sizes, a suitable number of particles can be expected to be oriented in such ways as to fulfil the Bragg condition for diffraction from every possible interplanar spacing. This improves the quality of the XRD data by improving the particle statistics. Preferably the sample is fed onto a carrier having an endless groove at a rate such that the groove is overfilled, in which case excess sample is removed from the carrier and the sample in the groove suitably presented for packing thereinto.

According to a second aspect the invention provides a method for continuously presenting a sample from a stream of particulate material containing crystalline substances for obtaining X-ray diffraction analyses of the particulate material, including (i) extracting a sample flow from the stream of particulate material, (ii) feeding the sample flow onto a continuously moving carrier and smoothing and flattening its surface, (iii) continuously moving the carrier to move the sample through a station for performing X-ray diffraction measurements on said flat and smooth sample surface, and (iv) continuously removing the sample from the carrier prior to feeding further sample flow onto the carrier.

According to a third aspect, the invention provides apparatus for analysing a stream of particulate material containing crystalline substances, including means for extracting a sample flow from the stream of particulate material, means for preparing the sample flow for X-ray diffraction measurements and conveying the so prepared sample flow through a measurement station, a measurement station including an X-ray generator and position sensitive detector for detecting X-ray diffraction patterns from the prepared sample flow, processor means for analysing the X-ray diffraction patterns to determine a composition for crystalline substances in the sample from each diffraction pattern and for providing a series of sequential composition determinations, thereby representing the composition of crystalline substances in the stream of particulate material.

Preferably the position sensitive detector for taking X-ray diffraction patterns of the sample is a curved position sensitive detector or area detector capable of simultaneous collection of a wide angular range of the x-ray diffractogram, rather than a sequential position sensitive detector for establishing a diffractogram in a series of measurements.

Preferably the means for preparing the sample flow includes a carrier for receiving the extracted sample flow, the carrier being drivable for continuous movement, and means for smoothing and flattening the surface of the sample on the carrier as the carrier moves and prior to the carrier conveying the sample flow through the measurement station.

Preferably the carrier includes an endless groove and said means for smoothing and flattening the surface of the sample packs the sample into the groove.

Preferably the means for smoothing and flattening the surface of the sample is a driven roller positioned over the endless groove.

Preferably the apparatus includes means for removing excess sample from the carrier prior to said means for smoothing and flattening the surface of the sample packing the sample into the endless groove. This means may be a scraper and vacuum apparatus.

Preferably the carrier is formed for the sample to be removed therefrom, or the apparatus includes means for removing the sample therefrom, prior to where the carrier receives the extracted sample flow and after the sample passes the measurement station.

Preferably the carrier is a horizontal wheel mounted for rotation about a vertical axis, and the endless groove is an annular groove in an upper surface of the wheel.

Preferably the apparatus includes means for removing the sample from the carrier prior to where the carrier receives the extracted sample flow, which means for removing the sample may include a scraper and vacuum apparatus.

The method may be performed on (and the apparatus positioned for) cement clinker which exits the kiln, in which case some of the clinker may be cooled and crushed to a powder to provide the stream of particulate material from which a sample is continuously extracted and fed onto the carrier.

The method may also or alternatively be performed on (and the apparatus positioned for) cement powder which exits the finish mill. Using this invention, extra grinding of the ex-mill cement sample is not required because the moving sample presented to an X-ray diffraction machine ensures that even with larger particle sizes, a suitable number of particles can be expected to be oriented in such ways as to fulfil the Bragg condition for diffraction from every possible interplanar spacing in a manner that accurately represents an XRD powder pattern.

The continuous withdrawal of a sample from the process stream allows its analysis on a continuous basis and thus the provision of substantially real time or current product data on which decisions can be made to control the process. Such control may be effected automatically, for example as in a closed loop feedback system, or manually by a process operator.

The term "continuous" and similar terms such as "continuously" or "continually" as used herein, are to be understood as meaning that the steps or measurements as so qualified apply for the duration of a discrete measurement cycle, which cycle may not be continuous in itself. That is, the invention encompasses the use of a number of sequential and discrete measurement cycles, with the above described steps of the method applying for each discrete cycle, as well as a measurement cycle which is long term and thus may be said to be "continuous" in itself.

According to a fourth aspect, the invention provides apparatus for presenting a sample from a stream of particulate material for X-ray diffraction measurements, including, a carrier for receiving a continuous feed of the material, the carrier being drivable for continuous movement, means for preparing the sample on the carrier and for smoothing and flattening its surface, and wherein the carrier is such that the said sample is removed, or the apparatus includes means for removing said sample therefrom, as the carrier moves, the removal of the sample occurring prior to where the carrier receives the feed of sample and after the sample passes a measurement station.

Although the carrier is preferably a horizontally orientated wheel or table which is mounted for rotation about a vertical axis, with the above-mentioned endless groove being an annular groove in an upper surface thereof, other configurations for the carrier are possible, for example an endless belt type conveyor which may have a longitudinal groove in its outer facing surface. For a carrier in the form of a rotatable carrier, the apparatus will include means for removing the packed sample from the carrier groove, which means may be an appropriately shaped stationary scraper for scooping the groove clean as the carrier rotates, or a suitable suction device or a combination of both. For a carrier in the form of an endless conveyor, the sample may fall off as the conveyor turns through 180° to follow its return path and may additionally include an appropriate scraper or other device to assist removal of the sample.

The packing of the sample into the endless groove accompanied by a smoothing and flattening of its surface is preferably accomplished by a driven roller which is positioned over the endless groove. The apparatus preferably further includes a rotatable brush for cleaning the roller. However the invention encompasses other forms of devices for such packing, for example a spatula.

XRD analysis of minerals is only able to analyse the crystals of the material largely at the surface of the sample presented to the XRD instrumentation and as the focus of the X-ray beam on the sample is tight, for example an area of the order of 4 mm$^2$, the more sample that is presented for analysis, the higher the confidence that the result is representative of the material in the process stream. The present invention, in providing a continuous sample supply, is a significant improvement over the above described prior art where only a single pellet of a few grams is periodically prepared and analysed. It is also important for accuracy that the sample surface be very smooth and flat, for example for a sample of powder which gives a residue on a 40 micron screen of less than 20% and can be delivered for analysis at less than 100° C., the surface should be smooth and flat to within 10 microns. The preferred form of device for packing and flattening the sample within the endless groove, namely a driven roller, provides for such accuracy.

BRIEF DESCRIPTION OF DRAWINGS

For a better understanding of the invention and to show how it may be carried into effect, an embodiment thereof will now be described, by way of non-limiting example only, with reference to the accompanying drawings, in which:

FIG. 2 is typical output results for XRD analysis of cement in tabular form.

DETAILED DESCRIPTION

Figure 1:
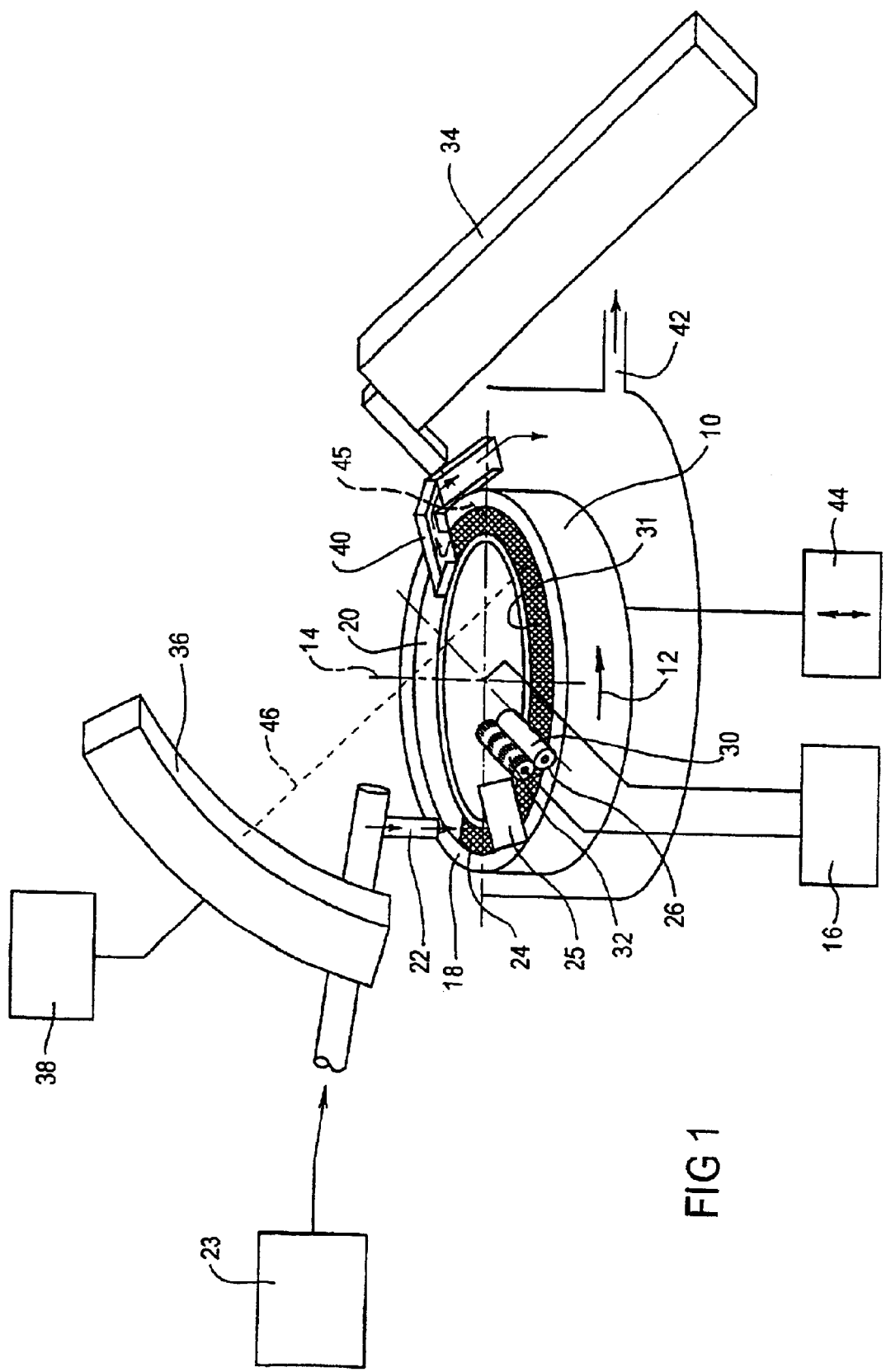
FIG. 1 is a side, perspective, diagrammatic representation of the main components of an example apparatus according to the present invention.

With reference to FIG. 1, the schematically illustrated apparatus includes a carrier in the form of a horizontally orientated wheel 10 which is mounted for rotation in an anti-clockwise direction 12 about a vertical axis 14 by a driving means 16. The wheel 10 includes a flat upper surface 18 in which an annular groove 20 is formed. A feeding means 22 is located for continuously feeding a particulate sample flow 24 onto surface 18 to overfill groove 20 as wheel 10 rotates. A scraper blade 25 is located to remove excess sample from the surface 18 prior to the sample being packed into the groove 20. A means 23 for continuously extracting the sample flow 24 from a stream of particulate material may comprise a screw or pneumatic conveyor or a combination of both, or other suitable extraction apparatus as will be known by a skilled person.

Means for packing the sample 24 into the groove 20 and smoothing and flattening its surface is a driven roller 26 which is located above the groove 20. Roller 26 is also driven for rotation in an anti-clockwise direction by driving means 16. The outer facing curved surface 30 of roller 26 is precision ground and the roller is driven such that the speed of surface 30 is the same as that of surface 18 at the groove 20. Thus the roller presses on the sample surface as presented from scraper 25 to pack the sample 24 into the groove 20 and provide it with a smooth and flat surface 31 to the desired accuracy without any speed differential between that surface 31 and the contacting surface 30. A roller brush 32 is also provided to clean the precision surface 30 of roller 26 to remove any sample that may adhere to it.

The wheel 10 then moves through a measurement station which includes an X-ray generator 34 and a position sensitive detector in the form of an area detector 36. A suitable processor means 38 presents the measurements in a desired format. Use of an area detector is preferred, although use of other types of detector, such as a single point detector combined with a goniometer to measure angular displacement, is possible. The area detector may collect the diffractogram over an angle of 120° 2θ. The X-ray diffraction instrumentation or diffractometer includes other components such as a tube stand and X-ray beam conditioning devices. Componentry for this instrumentation is described in more detail below.

Following its passage through the measurement station, the sample 24 in groove 20 is removed by a scraper arrangement 40 prior to further sample 24 being fed onto the carrier wheel 10. The sample material which is removed from carrier wheel 10 by scrapers 23 and 40 is collected and extracted from the apparatus for example by a vacuum device as represented by reference 42.

Carrier 10 also includes a precision height adjustment device 44 as accurate positioning of the surface 31 of the bed of sample 24 is required for the X-ray diffraction analysis as represented by line 45 for an incident X-ray beam and line 46 for the diffracted rays.

Example XRD instrumentation consists of the following
 (i) INEL 3 kw X-ray generator (34) with RS232 interface to power the XRD tube.
 (ii) Philips, cobalt target, long fine focus XRD tube rated at 1800 W.
 (iii) Graphite monochromator to remove unwanted wavelengths and 0.2×8 mm slits to define the beam size at the sample.
 (iv) INEL CPS120 area detector (36) to detect the XRD pattern plus a panel of electronics to process signals from the detector.
 (v) Industrial computer (38) built into the system to control data collection, analysis and result reporting.

Data is collected using software specifically designed and coded for interaction with the INEL detector 36. Data can be collected for times ranging from 1 to 1000 seconds and summed over as many data sets as deemed necessary to obtain appropriate counting statistics. One example of such settings are 60 second data collections with 10 data sets summed for analysis providing analyses every minute after the first 10 minutes.

The XRD data is analysed using the "whole pattern" or Rietveld based approach. FIG. 2 is a table of typical output results.

The apparatus of the invention is preferably located (and consequently the method performed) in an airconditioned room to avoid instrument distortion due to temperature changes and to ensure protection of the electronic equipment. A representative sample of a product stream can be conveyed into such a room located in proximity to the product stream. The invention is suitable for any process stream that can be reduced to a dry powder form (for example with a residue on a 40 micron screen of less than 20%). Preferably such powder would be delivered to the XRD instrument at less than 100° C.

The invention described herein is susceptible to variations, modifications and/or additions other than those specifically described and it is to be understood that the invention includes all such variations, modifications and/or additions which fall within the scope of the following claims.

What is claimed is:

1. A method for analysing a stream of particulate material containing crystalline substances including
    i) extracting a sample flow from the stream of particulate material,
    (ii) smoothing and flattening a surface of said sample flow to prepare said sample flow for X-ray diffraction measurements,
    (iii) directing an X-ray beam onto the smoothed and flattened surface of the sample flow as it passes through a measurement station and detecting diffracted X-rays over an angular range to provide a diffraction pattern,
    (iv) analysing the diffraction pattern to determine a composition for crystalline substances in the sample,
    (v) repeating step (iii) to provide diffraction patterns from the continuously moving sample at predetermined intervals, and
    (vi) repeating step (iv) for each diffraction pattern from step (v),
    whereby a series of sequential composition determinations from the sample flow are provided which represent the composition of crystalline substances in the stream of particulate material.

2. A method as claimed in claim 1 wherein the diffracted X-rays of step (iii) are simultaneously detected over the angular range.

3. A method as claimed in claim 2 wherein the diffraction patterns are analysed using a whole pattern analysis method.

4. A method as claimed in claim 3 wherein the diffraction patterns are analysed using the Rietveld method.

5. A method as claimed in claim 1 wherein step (ii) includes,
    feeding the sample onto a continuously moving carrier and smoothing and flattening its surface.

6. A method as claimed in claim 5 wherein the sample is formed into a bed on the moving carrier.

7. A method as claimed in claim 6 wherein the carrier includes an endless groove for receiving the sample and the sample is packed into the groove to form the bed.

8. A method as claimed in claim 5 wherein following step (iii) the sample is continuously removed from the carrier prior to feeding further sample onto the carrier.

9. A method as claimed in claim 1 wherein the stream of particulate material is cement clinker and the method includes a step of cooling and crushing a portion of the cement clinker to provide the sample flow.

10. A method as claimed in claim 1 wherein the stream of particulate material is cement.

11. A method for continuously presenting a sample from a stream of particulate material containing crystalline substances for obtaining X-ray diffraction analyses of the particulate material, including
    (i) extracting a sample flow from the stream of particulate material,
    (ii) feeding the sample flow onto a continuously moving carrier and smoothing and flattening its surface,
    (iii) continuously moving the carrier to move the sample through a station for performing X-ray diffraction measurements on said flat and smooth sample surface, and
    (iv) continuously removing the sample from the carrier prior to feeding further sample flow onto the carrier.

12. Apparatus for analysing a stream of particulate material containing crystalline substances, including
    means for extracting a continuous sample flow from the stream of particulate material,
    means for smoothing and flattening a surface of said continuous sample flow to prepare the continuous sample flow for X-ray diffraction measurements,
    a measurement station including an X-ray generator and position sensitive detector for detecting X-ray diffraction patterns from the prepared continuous sample flow,
    processor means for analysing the X-ray diffraction patterns to determine a composition for crystalline substances in the sample from each diffraction pattern and for providing a series of sequential composition determinations, thereby representing the composition of crystalline substances in the stream of particulate material.

13. Apparatus as claimed in claim 12 wherein the position sensitive detector of the measurement station is a curved position sensitive detector for simultaneously detecting diffracted X-rays over an angular range.

14. Apparatus as claimed in claim 12 wherein the position sensitive detector is an area detector.

15. Apparatus as claimed claim 12 wherein the means for smoothing and flattening a surface of the sample flow includes a carrier for receiving the extracted sample flow, the carrier being drivable for continuous movement, whereby said means for smoothing and flattening the surface of the sample operates on the carrier as the carrier moves and prior to the carrier conveying the sample flow through the measurement station.

16. Apparatus as claimed in claim 15 wherein the carrier includes an endless groove and said means for smoothing and flattening the surface of the sample packs the sample into the groove.

17. Apparatus as claimed in claim 16 wherein said means for smoothing and flattening the surface of the sample is a driven roller positioned over the endless groove.

18. Apparatus as claimed in claim 17 including means for removing excess sample from the carrier prior to said means for smoothing and flattening the surface of the sample packing the sample into the endless groove.

19. Apparatus as claimed in claim 18 wherein said means for removing excess sample includes a scraper and vacuum apparatus.

20. Apparatus as claimed in claim 15 wherein the carrier is formed for the sample to be removed therefrom, or the apparatus includes means for removing the sample therefrom, prior to where the carrier receives the extracted sample flow and after the sample passes the measurement station.

21. Apparatus as claimed in claim 16 wherein the carrier is a horizontal wheel mounted for rotation about a vertical axis, and the endless groove is an annular groove in an upper surface of the wheel.

22. Apparatus as claimed in claim 20 wherein the apparatus includes means for removing the sample from the carrier prior to where the carrier receives the extracted sample flow, which means for removing the sample includes a scraper and vacuwn apparatus.

23. Apparatus for presenting a sample from a stream of particulate material for X-ray diffraction measurements including,
 a carrier for receiving a continuous feed of the particulate material, the carrier being drivable for continuous unidirectional movement, and
 means for preparing the sample on the carrier and for smoothing and flattening the surface of said sample,
 wherein the carrier is such that said sample is removed, or the apparatus includes means for removing said sample therefrom, as the carrier moves, the removal of the sample occurring prior to where the carrier receives the feed of sample and after the sample passes a measurement station.

* * * * *

UNITED STATES PATENT AND TRADEMARK OFFICE
CERTIFICATE OF CORRECTION

PATENT NO.   : 6,735,278 B2
DATED        : May 11, 2004
INVENTOR(S)  : Ian Charles Madsen et al.

It is certified that error appears in the above-identified patent and that said Letters Patent is hereby corrected as shown below:

Column 8,
Line 31, after "claimed" insert -- in --.

Signed and Sealed this

Thirtieth Day of November, 2004

JON W. DUDAS
*Director of the United States Patent and Trademark Office*